United States Patent [19]

Horbaschek

[11] Patent Number: 5,412,704
[45] Date of Patent: May 2, 1995

[54] X-RAY DIAGNOSTICS INSTALLATION HAVING A VARIABLE APERTURE DIAPHRAGM AND METHOD FOR OPERATING SAME

[75] Inventor: Heinz Horbaschek, Erlangen, Germany

[73] Assignee: Siemens Aktiengesellschaft, Munich, Germany

[21] Appl. No.: 283,191

[22] Filed: Aug. 4, 1994

[30] Foreign Application Priority Data

Aug. 26, 1993 [DE] Germany .................. 43 28 783.2

[51] Int. Cl.$^6$ ............................................. H05G 1/64
[52] U.S. Cl. ................................. 378/98.2; 378/151; 378/160
[58] Field of Search .............. 378/98.2, 98.5, 98.6, 378/98.7, 98.12, 151, 160

[56] References Cited

U.S. PATENT DOCUMENTS 5,194,726 3/1993 Jonkman ........................ 378/98.2
5,287,396 2/1994 Stegehuis ....................... 378/98.2

Primary Examiner—David P. Porta
Assistant Examiner—Don Wong
Attorney, Agent, or Firm—Hill, Steadman & Simpson

[57] ABSTRACT

An x-ray diagnostics installation includes an x-ray tube, a variable aperture diaphragm, and an x-ray image intensifier video chain which includes an x-ray image intensifier, a video pick-up unit, a processing circuit, and a playback unit. The variable aperture diaphragm has a central region and an outer region which exhibit different x-ray transparencies. When adjusted to a first position, the aperture diaphragm permits x-rays to pass only through said central region unattenuated. The aperture diaphragm is adjusted to a second position for every $n^{th}$ image, wherein both the central region and the outer region permit x-rays to pass through the diaphragm unattenuated. Each $n^{th}$ image is entered into an image memory connected to the video pick-up unit and is superimposed on an image produced when the diaphragm is in the first position.

22 Claims, 2 Drawing Sheets

X-RAY DIAGNOSTICS INSTALLATION HAVING A VARIABLE APERTURE DIAPHRAGM AND METHOD FOR OPERATING SAME

BACKGROUND OF THE INVENTION

1. Field of the Invention

The present invention is directed to an x-ray diagnostics installation of the type having an x-ray tube, a variable aperture diaphragm and an x-ray image intensifier video chain which includes an x-ray image intensifier, a video pick-up unit, a processing circuit and a playback unit, as well as to a method for operating such an x-ray diagnostics installation. The apparatus and method serve the purpose of reproducing attenuated x-ray images.

2. Description of the Prior Art

The flow density of x-ray photons in x-ray diagnostics installations of the type generally described above is usually uniform over the cross-section of the x-ray beam of the x-ray source. The flow density is dependent on the required image quality, and defines the radiation load on the patient. If, however, only one person observes the monitor (playback unit), the x-ray photon flow is utilized only at the location at which the observer is looking at the moment with foveal vision. The human eye has much less capacity for resolution outside of this small foveal region. The patient can thus be irradiated with a lower flow density in a region of the image field outside of this small region which corresponds to the foveal region of the eye. The overall radiation load on the patient is thereby reduced.

For this reason, an aperture diaphragm is disclosed in German OS 27 40 998 which permits intensive x-rays to pass there through in a central region, whereas x-rays are attenuated in an outer region surrounding the central region. In order to insure that the observation area of the observer coincides with the region of intense irradiation, an apparatus is provided which determines the direction in which the observer is looking, and causes a corresponding shift in the aperture diaphragm. Such an acquisition of the viewing direction, however, is extremely difficult in practice.

If it is assumed, however, that the principal viewing direction of an observer will lie in the middle of the x-ray image, the diaphragm could be stationarily arranged, and the full image quality would then be present in the central region. A substantially poorer image quality, by contrast, occurs in the outer region of the image field, and this portion of the region can therefore only serve for the purpose of an overview, and cannot be used for detailed diagnostic purposes. A significant disadvantage of this known technique is the difference in the image character between the central region and the surrounding field. In the surrounding field, either a substantially higher noise level is present or, if a chronological filtering for noise reduction is undertaken, a substantially more pronounced smearing of moving subjects will be present.

SUMMARY OF THE INVENTION

It is an object of the present invention to provide an x-ray diagnostics installation of the type generally initially described, wherein the radiation load on a patient is reduced but with an unaltered image quality.

It is a further object of the present invention to method for operating an x-ray diagnostics installation of the type generally initially described which enables the radiation load on the patient to be reduced while producing an image having an unaltered image quality.

These objects are achieved in accordance with the principles of the present invention in an x-ray diagnostics installation, and in a method for operating such an installation, wherein the aperture diaphragm has a central region and an outer region having respectively different x-ray transparencies, and wherein the aperture diaphragm is operated so that it assumes a first position wherein x-rays pass unattenuated only through the central region and is then entirely opened in a second position for every $n^{th}$ image, so that both the central region and the other region permit x-rays to pass there through unattenuated. Each $n^{th}$ image is entered into an image memory connected to the video pick-up unit. An image of the central region is thus reproduced at a nominal (normal) number of frames per second (image frequency), whereas the radiation load in the outer region is reduced as a result of the lower number of frames per second (image frequency) produced when the outer region is opened.

A simultaneous display of the respective images produced with the aperture in the first and second positions ensues by providing a mixer stage wherein the stored image, produced with the aperture in the second position, and a chronologically following image, produced with the aperture in the first position, are superimposed. Separate observation of the images is enabled when the current image is reproduced on a first monitor, and the stored image is reproduced on a second monitor.

Preferably the x-ray tube is operated in a pulsed manner by a suitable control circuit.

The aperture diaphragm may be in the form of a variable pinhole diaphragm, such as an iris diaphragm or a series of pinholes of different diameters disposed in a carrier which is movable in the path of the x-ray beam. The aperture diaphragm can be transparent for x-rays in the central region and can be partially transmissive in the outer region (in the first position), in which case the outer region may have an x-ray attenuation which increases continuously from the inner portion of the outer region, surrounding the central region, to the periphery of the outer region. Alternatively, the aperture diaphragm can be transparent for x-rays in its central region and opaque for x-rays in its outer region (in the first position).

It has proven advantageous for the number n to assume values from 5 through 20, preferably a value of 10.

A image reproduction which is adapted to a particular motion of the subject, or an organ of the subject, can ensue when a motion detector is provided which controls the number n. The recognition of the motion can ensue in the central region and/or in the outer region of the image.

DESCRIPTION OF THE PREFERRED EMBODIMENTS

Figure 1:
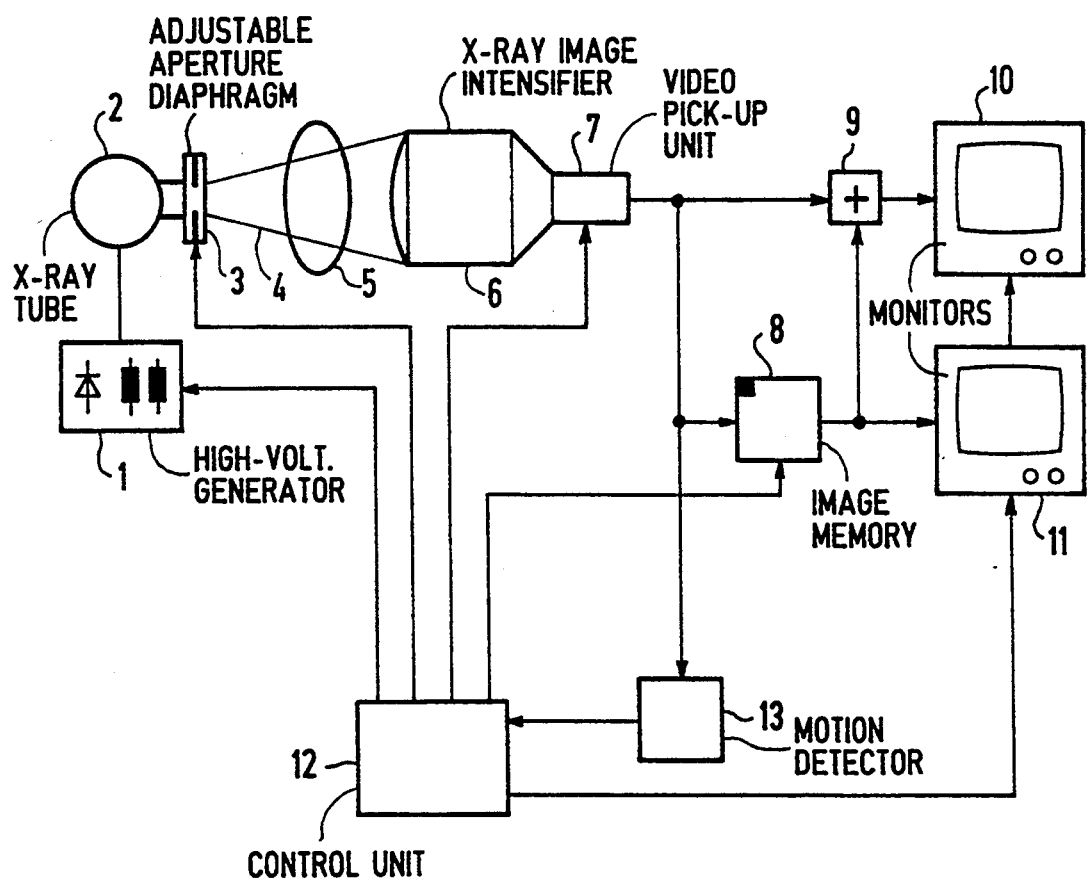
FIG. 1 is a schematic blocked diagram of an x-ray diagnostics installation constructed and operating in accordance with the principles of the present invention.

An x-ray diagnostics installation is shown in FIG. 1 which includes a high-voltage generator 1 connected to an x-ray tube 2. An aperture diaphragm 3 is disposed at the exit window of the x-ray tube 2 in the path of the x-rays emitted by the x-ray tube 2, for gating the x-ray beam 4 which penetrates a patient 5. The x-ray beam 4, attenuated by the patient 5 in accordance with the patient's transparency, is incident on the input luminescent screen of an x-ray image intensifier 6, which converts the x-ray image into a smaller, visible image intensified in brightness. The visible image is acquired by a video pick-up unit 7 optically coupled to the x-ray image intensifier 6, and is converted into a video signal. The video signal from the video pick-up unit 7 is supplied to an image memory 8 and to an addition stage 9, serving as a mixer, wherein, as described below, the stored image and the current video signal are superimposed. The output of the addition stage 9 is supplied to a first monitor 10 for playback. A second monitor 11 for playback of the stored image can also be connected to the image memory 8. A control unit 12 is connected to the high-voltage generator 1, to the aperture diaphragm 3, to the video pick-up unit 7, to the image memory 8 and to the monitors 10 and 11 for control, synchronization and clocking of those components.

Figure 2:
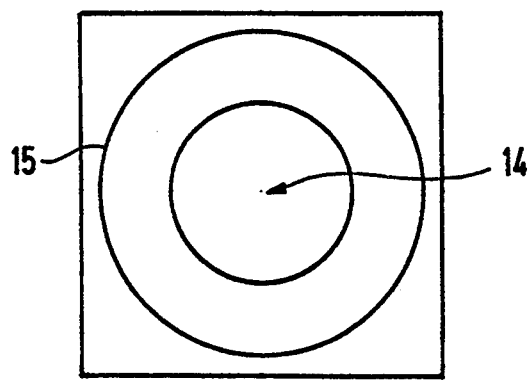
FIG. 2 is a plan view showing the structure of an aperture diaphragm for use in the apparatus of FIG. 1.

The variable aperture diaphragm 3, whose division is shown in FIG. 2, has a central region 14 and an outer region 15. The central region 14 may be in the form of a pinhole diaphragm, and gates a small but intense x-ray beam. The outer region 15 is either completely opaque to x-rays, or exhibits an x-ray attenuation which increases from its inner portion toward its periphery. A corresponding attenuation of the x-rays emitted by the x-ray tube 2 thereby ensues, so that the portion of the overall image produced by x-rays passing through the central region 14 is reproduced with high image quality, and the portion of the overall image produced by x-rays passing through the outer region 15 is reproduced either with low image quality, or without a contribution to the image of the patient (i.e., as a completely black region).

Figure 3:
FIG. 3 shows the clock sequence for the control device for operating the x-ray tube in the installation of FIG. 1.

The x-ray tube 2 can be operated in a pulsed manner, using the clock signal shown in FIG. 3 supplied to the high voltage generator 1 by the control unit 12.

In order to reproduce an overall image having a high image quality on the monitor 10, the aperture diaphragm 3 is completely opened at every $n^{th}$ x-ray pulse, so that an overall image with constant image quality is produced. Under the control of the control unit 12, this image is entered into the image memory 8 and is thus present at the output of the image memory 8 until the next pulse which is a multiple of the number n. The stored image and the current images of the x-ray beam 4 attenuated by the aperture diaphragm 3 which follow the stored image can be mixed in the addition stage 9.

The image produced when the outer region 15 does not attenuate the x-rays (i.e., when the aperture diaphragm 3 is in the second position) is produced at a relatively low frequency compared to the production of images when the aperture 3 is in the first position. The image produced when the aperture diaphragm 3 is in the second position is thus retained for reproduction in the digital image memory 8 and is repeatedly read out until it is regenerated (refreshed). The image produced with the aperture diaphragm in its first position, i.e., with only x-rays passing through central region 14 being unattenuated, is continuously renewed. This means that images obtained using x-rays passing through the central region 14 of the diaphragm 3 are obtained at the standard number of frames per second (image frequency) of, for example, 25I/s or 30I/s. The images produced with x-rays unattenuated by the outer region 15 are produced with a significantly reduced number of frames per second (image frequency) of, for example, 2.5I/s or 3I/s.

Due to the storage and superimposition of the images produced using x-rays unattenuated by the outer region 15, however, the image quality, and thus the image character, are in conformity over the entire image field with respect to noise and sharpness. If no movements of the overall subject are present, barely any difference between the outer region and the central region of the resulting image can be recognized. A dose reduction of approximately one-third of the normal dose, however, can be used as a result of these measures.

Figure 4:
FIGS. 4–6 respectively illustrates x-ray images produced in accordance with the principles of the present invention.
Figure 5:
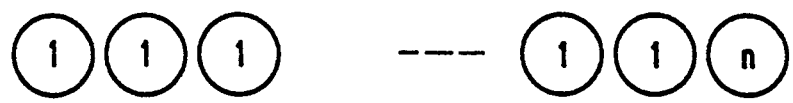
Figure 6:
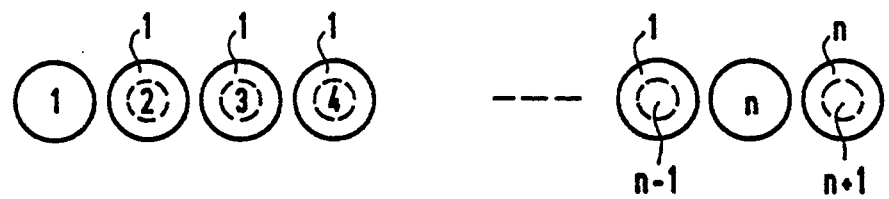

The conditions for gating are symbolically represented in FIGS. 4–6. FIG. 4 shows the size of the x-ray beam 4 gated by the diaphragm 3, and thus shows the size of the image field. The first image has the full size, whereas the subsequent images, up to the image having number n, contain only the central region 14 gated by the diaphragm 3. The stored image is shown in FIG. 5, having the full size and displayable, for example, by itself at the second monitor 11. The superimposition is graphically shown in FIG. 6. The first image is simultaneously stored and reproduced on the monitor 10. A superimposition of the edge region of the first image with the gated image region of the second region is indicated by the dashed lines, and is continues up to the image having number n−1. The $n^{th}$ image is then read into the image memory 8, and is subsequently mixed with the image n+1 in the center.

The number n can assume any desired value. A greater radiation reduction, with a simultaneous increase in the degree to which the image stored in the image memory 8 is (out-of-date) are obtained as an increase. Given a small value for n, by contrast, the overall image can quickly follow movements of the subject, and even though the radiation load on the patient is less then the load which would occur without using the invention, it is still relatively high. The number n can assume values between 5 and 20, but preferably has the value 10. The value for the number n can be set by manually operable means or, as described below, can be varied through the use a motion detector.

If the subsequent images are composed only of a part of the central region 14, the mixing can ensue so that the central region 14 of the composite image is formed only by the current image and the outer region 15 of the composite image is formed only by the stored image. It is also possible, however, to compose the central region 14 by mixing the current and the stored image.

If, by contrast, the subsequent images are composed of the central region 14 as well as the attenuated outer region 15, mixing can ensue such that both the central region 14 and the outer region 15 of the composite image are formed by the current image and the stored image. In this case, the outer region 15 is not completely opaque for x-rays, but merely attenuates the x-rays. The attenuation can be uniform, or can increase continuously from an interior of the region 15 to its periphery.

The x-ray diagnostics installation of the invention can also include a motion detector 13. Given pronounced chronological variations in the video signal due to movements of the subject, the video signal of the video pick-up unit 7 can be supplied to the motion detector 13. The motion detector 13 can then undertake motion measurements either in the central region 14 or in the outer region 15, these measurements then effecting a control of the number n. This can be achieved by triggering the entry of a new image into the image memory 8 immediately upon the detection of a specified motion, or a specified degree of motion. This results in substantially no jumping of the image occurring in the case, for example, of displacement of the patient table or motion of the gantry. An ECG triggering of the number of frames per seconds is also possible.

The exemplary embodiment of the invention disclosed herein provides an x-ray diagnostics installation wherein the radiation load on the patient is reduced but an image is achieved having the same image quality as would be obtained using a higher radiation load, with the outer region 15 of the image only serving the purpose of orientation in the overall image.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray diagnostics installation comprising:
   an x-ray tube which emits x-rays;
   an adjustable aperture diaphragm, having a central region and an outer region surrounding said central region, disposed for gating said x-rays, said diaphragm being suitable at a first aperture position wherein only x-rays in said central region pass unattenuated through said diaphragm and at a second aperture position wherein x-rays pass through both said central and outer regions unattenuated;
   means for producing a series of x-ray images of a subject from x-rays gated by said diaphragm;
   means for producing a respective video signal corresponding to each x-ray image;
   means for converting each video signal into a digital image;
   means for operating said diaphragm to set said diaphragm at said second aperture position for every $n^{th}$ x-ray image and for otherwise setting set diaphragm at said first aperture position;
   means for storing the digital image corresponding to said $n^{th}$ x-ray image; and
   means for displaying the stored image and an image obtained with said diaphragm at said first position.

2. An x-ray diagnostics installation as claimed in claim 1, further comprising means for mixing said stored image with an x-ray image obtained immediately chronologically following said stored image, and wherein said means for displaying comprises means for displaying said stored image and said immediately chronologically following image superimposed.

3. An x-ray diagnostics installation as claimed in claim 1, wherein said means for displaying includes a first monitor and a second monitor with said stored image being displayed on said first monitor and a current image obtained with said diaphragm at said first position being displayed on said second monitor.

4. An x-ray diagnostics installation as claimed in claim 1, wherein said means for producing a series of x-ray images comprises control means for operating said x-ray tube in a pulsed manner with one x-ray image being generated each time said x-ray tube is pulsed.

5. An x-ray diagnostics installation as claimed in claim 1, wherein said adjustable aperture diaphragm comprises a variable pinhole diaphragm.

6. An x-ray diagnostics installation as claimed in claim 1, wherein said adjustable aperture diaphragm comprises a diaphragm having a central region transparent for x-rays and an outer region which is partially transmissive for x-rays.

7. An x-ray diagnostics installation as claimed in claim 1, wherein said adjustable aperture diaphragm comprises an outer region having an inner portion and a periphery and having an x-rays attenuation which continuously increases from said inner portion to said periphery.

8. An x-ray diagnostics installation as claimed in claim 1, wherein said adjustable aperture diaphragm comprises a central region which is transparent for x-rays and an outer region which, in said first position, is opaque for x-rays.

9. An x-ray diagnostics installation as claimed in claim 1, wherein said means for operating said diaphragm comprises means for operating said diaphragm to set said diaphragm at said second aperture position for each x-ray image in a range from each fifth x-ray image to each 20th x-ray image, and for otherwise setting said diaphragm at said first aperture position.

10. An x-ray diagnostics installation as claimed in claim 1, wherein said means for operating said diaphragm comprises means for operating said diaphragm to set said diaphragm at said second aperture position for each tenth x-ray image and for otherwise setting said diaphragm at said first aperture position.

11. An x-ray diagnostics installation as claimed in claim 1, further comprising means for detecting motions in said x-ray images and for setting a value for n dependent on said motion.

12. An x-ray diagnostics installation as claimed in claim 11, wherein said means for detecting motion comprises means for detecting motion in a region of each x-ray image produced by x-rays from said central region of said diaphragm.

13. An x-ray diagnostics installation as claimed in claim 11, wherein said means for detecting motion comprises means for detecting motion in a region of each x-ray image produced by x-rays from said outer region of said diaphragm.

14. A method for operating an x-ray diagnostics installation comprising the steps of:
   emitting x-rays from an x-ray tube;
   gating said x-rays with an adjustable aperture diaphragm, having a central region and an outer region surrounding said central region, by setting said diaphragm at a first aperture position wherein only x-rays in said central region pass unattenuated through said diaphragm and at a second position wherein x-rays pass through both said central and outer regions unattenuated;
   producing a series of x-ray images of a subject from x-rays gated by said diaphragm;
   producing a respective video signal corresponding to each x-ray image;
   converting each video signal into a digital image;
   operating said diaphragm to set said diaphragm at said second aperture position for every small $n^{th}$ x-ray image and otherwise setting said diaphragm at said first aperture position;
   storing the digital image corresponding to said $n^{th}$ x-ray image; and displaying the stored image and an image obtained with said diaphragm at said first aperture position.

15. A method as claimed in claim 14 comprising the additional step of mixing said stored image and a current image obtained with said diaphragm at said first aperture position, and wherein the step of displaying comprises displaying said stored image and said current image superimposed.

16. A method as claimed in claim 14 wherein the step of displaying comprises displaying said stored image on a first monitor and displaying said image obtained with said diaphragm at said aperture position on a second monitor.

17. A method as claimed in claim 14 wherein the step of producing a series of x-ray images comprises operating said x-ray tube in a pulsed manner and producing an x-ray image each time said x-ray tube is pulsed.

18. A method as claimed in claim 14 comprising the additional step of selecting n in a range between 5 and 20.

19. A method as claimed in claim 14 comprising the additional step of selecting n to be 10.

20. A method as claimed in claim 14 comprising the additional step of detecting motion in said x-ray images and controlling a value of n dependent on said motion.

21. A method as claimed in claim 20 wherein the step of detecting motion in said images comprises detecting motion in a portion of each image produced from x-rays passing only through said central region of said diaphragm.

22. A method as claimed in claim 20 wherein the step of detecting motion in said images comprises detecting motion in a portion of each image produced from x-rays passing only through said outer region of said diaphragm.

* * * * *